United States Patent [19]

Konishi et al.

[11] Patent Number: 4,836,859

[45] Date of Patent: Jun. 6, 1989

[54] METHOD FOR TREATING CONTACT LENSES

[75] Inventors: Akihiko Konishi, Kashiwa; Masamichi Mizukami; Masanori Shimuta, both of Tokyo, all of Japan

[73] Assignee: Mitsubishi Gas Chemical Co., Ltd., Tokyo, Japan

[21] Appl. No.: 149,628

[22] Filed: Jan. 28, 1988

[30] Foreign Application Priority Data

Feb. 6, 1987 [JP] Japan .................................. 62-24767

[51] Int. Cl.$^4$ ................................................ B08B 3/10
[52] U.S. Cl. ......................................... 134/1; 134/27; 134/42; 422/20; 422/128

[58] Field of Search ........................... 134/1, 2, 27, 42; 422/20, 128

[56] References Cited

U.S. PATENT DOCUMENTS 4,187,868  2/1980  Rudolphi ............................... 134/1
4,382,824  5/1983  Halleck ................................... 134/1

*Primary Examiner*—Asok Pal
*Attorney, Agent, or Firm*—Ladas & Parry

[57] ABSTRACT

Contact lenses are treated with hydrogen peroxide and the remaining hydrogen peroxide is decomposed by electrolysis.

7 Claims, No Drawings

METHOD FOR TREATING CONTACT LENSES

BACKGROUND OF THE INVENTION

1. Field of the Invention

This invention relates to an improved method for treating contact lenses.

2. Description of the Related Art

While using contact lenses, dirt in the environment, microorganisms, proteins in tear liquid and the like attach to the lenses during wearing and eyes are hurt by them when the contact lenses are worn for a long time. Therefore, it is necessary to sterilize and wash the lenses periodically, preferably, every day.

It has been known that hydrogen peroxide can be effectively used for sterilizing and washing contact lenses. It is also known that the remaining hydrogen peroxide in the treating liquid after the treatment irritates and hurts eyes when the lenses thus treated are worn again and therefore, the remaining hydrogen peroxide must be removed.

There have been already proposed various means for removing hydrogen peroxide in processes for treating contact lenses with hydrogen peroxide. For example, U.S. Pat. No. 3,829,329 discloses boiling in a distilled water and normal saline solution. Such boiling is, however, inconvenient to the user and deteriorates contact lenses. Japanese Patent Application Laidopen Nos. Sho 59-105,457 and Sho 60-70,416 disclose that hydrogen peroxide is decomposed by using sodium pyruvate and sodium sulfite, respectively, as a reducing agent. In these methods the reducing agent should be used in the stoichiometrical amount or more, so that it is complicated to weigh the reducing agent and further the remaining reducing agent and the resulting oxidized product are contained in the treating liquid, and therefore, these compounds may adversely affect eyes. In addition, U.S. Pat. No. 4,414,127 discloses water-soluble inorganic salts or organic salts, in particular, copper sulfate, as a hydrogen peroxide decomposing catalyst, but even when such catalyst is used, metal ions are contained in the treating liquid so that it is difficult to avoid any adverse effect on eyes.

On the other hand, Japanese Patent Application Publication No. Sho 53-14,243 disclosed metallic catalysts for decomposing hydrogen peroxide, in particular, platinum black carrying catalyst. According to this method, indeed any problems found in the above-mentioned patents do not occur and this method appears to be good, but the platinum black carrying catalyst is produced by coating chloroplatinic acid on a carrier and reducing it, so that the production process is very complicated, and further the platinum black is easily peeled off from the carrier and lost by mechanical contact resulting in short life. Therefore, this method neither gives a satisfactory result.

SUMMARY OF THE INVENTION

An object of the present invention is to provide a simple and safe method for decomposing the remaining hydrogen peroxide in the treatment of contact lenses using hydrogen peroxide.

According to the present invention, there is provided a method for treating contact lenses with hydrogen peroxide which comprises electrolyzing the remaining hydrogen peroxide.

DESCRIPTION OF THE PREFERRED EMBODIMENTS

The present invention is concerned with a method for treating contact lenses with hydrogen peroxide comprising electrolyzing the remaining hydrogen peroxide. For example, contact lenses are soaked in an aqueous hydrogen peroxide in an optional vessel provided with electrodes for a desired period of time and then voltage is applied across the electrodes to decompose and remove the remaining hydrogen peroxide; or contact lenses are soaked in an aqueous hydrogen peroxide in an optional vessel provided with electrodes across which voltage has been applied to treat the contact lenses and the hydrogen peroxide is decomposed and removed.

The contact lenses thus treated are taken out and used without any further procedure, or, if desired, are washed with a physiological saline solution and then used again.

According to the present invention, when the concentration of hydrogen peroxide in the aqueous solution is high, the sterilization effect is large, but there is a fear that the contact lenses are deteriorated and when the hydrogen peroxide attaches to skin, it is hurt. On the contrary, when the concentration of hydrogen peroxide is low, the sterilization and washing effect is low. Therefore, the concentration of hydrogen peroxide is preferably 10–0.1 weight %, particularly, 5–0.5 weight %.

It is only necessary that the amount of the aqueous hydrogen peroxide is sufficient to treat the contact lenses by a soaking treatment. When the concentration of hydrogen peroxide is, for example, 3 weight %, a sufficient treatment can be effected by soaking the contact lenses for 5–10 minutes, but it is necessary to pay attention to the time required for removing sufficiently the remaining hydrogen peroxide though this time can be optionally set as mentioned later.

The aqueous hydrogen peroxide according to the present invention preferably contains a salt, that is, there is contained a salt at a concentration which gives an aqueous solution of 200–400 milliosmotic pressure mole (m Os)/kg substantially isotonic to the osmotic preasure of tear liquid of man.

A salt at such concentration is usually a 0.7–1.4 weight % solution of sodium chloride in an ordinary aqueous hydrogen peroxide. Salts other than sodium chloride may be any water-soluble salts as far as they have an affinity for tissues of eye. For example, there may be mentioned chlorides such as potassium chloride, magnesium chloride, calcium chloride and the like. In addition, salts present in tear liquid such as sodium carbonate, sodium phosphate, sodium sulfate, potassium sulfate and the like may be used.

The pH of the aqueous hydrogen peroxide is preferably 7.5–6.5, more preferably 7.1–6.9. Buffers can be used to maintain the pH. There may be used buffer systems such as a combination of sodium borate and boric acid, a combination of monosodium phosphate and disodium phosphate, and the like. In case of using such buffer system, it is also desirable that the total salt concentration is such that the osmotic pressure is isotonic to that of a tear liquid.

Further the aqueous hydrogen peroxide used in the present invention may contain a stabilizer for hydrogen peroxide. The stabilizer includes compounds ordinarily known as a stabilizer for hydrogen peroxide such as sodium polyphosphate, sodium stannate, sodium salt or ammonium salt of ethylenediaminetetraacetic acid.

Examples of conditions for electrolysis are as shown below. As the electrode material to which voltage is applied, (1) the material is stable to an aqueous hydrogen peroxide, (2) any electrochemical reaction does not occur in the electrode itself when voltage is applied, or even if an electrochemical reaction occurs, the degree is a little, and (3) upon passing electric current, a relatively low hydrogen peroxide decomposition voltage is produced which can decompose hydrogen peroxide only and causes only negligible degree of side electrolysis. Such electrode materials are, for example, as anode, platinum, gold, carbon, graphite and the like, and as cathode, platinum, gold, carbon, graphite, nickel, silver chloride and the like. Preferably, platinum, gold, carbon and graphite are used as both anode and cathode.

Among these electrode materials, noble metals such as, particularly, platinum, gold and the like, itself are said to have a catalytic activity capable of decomposing hydrogen peroxide according to the above-mentioned Japanese Patent Application Publication No. Sho 53-14,243. However, as a result of the present inventors' investigation, it has been found that the catalytic activity of noble metal can actually work only when, for example, in case of platinum, platinum is in the form of very fine particles such as platinum black or carried platinum and where commercially available platinum wire or platinum plate, that is, in the form of platinum mass as it is, the desired active state can not be attained.

As is clear from the working examples (infra), regardless of the shape of noble metal, that is, even when the noble metal can not exhibit practically a sufficient catalytic activity in the form of metal mass, in the case where the noble metal mass is used as electrodes and voltage is applied across the electrodes, hydrogen peroxide can be easily decomposed. This is a particular meritorious effect of the present invention. As is clear from the explanation as above, the shape and structure of the electrode are not particularly limited, for example, the electrode may take an optional form such as fiber, wire, rod, foil, film, plate and the like. The size may be appropriately determined taking the time required for decomposing hydrogen peroxide into consideration.

On the other hand, these electrode materials may be used in combination with an inert material which does not adversely affect the electrode materials. For example, an inert material having a wide contact area may be used, that is, there may be used a member constituted of an electrode material carried on a so-called support. As the inert material, there may be used, for example, inorganic compounds usually used as a carrier for electrode materials such as alumina, silica, silica-alumina, silica-magnesia, alumina-magnesia, zeolite, kaolinite and the like; thermoplastic resins such as polyethylene resins, polypropylene resins, polystyrene resins, polyvinyl chloride resins, polyacrylonitrile resins, polycarbonate resins, polyamide resins, polyester resins, polyphenylene oxide resins, and the like; and thermosetting resins such as phenolic resins, furan resins, unsaturated polyester resins, epoxy resins and the like.

There are various methods for preparing electrode materials using inorganic compounds as a support. There are, for example, a method which comprises simultaneously precipitating a metal ion to become the electrode material and an inorganic ion (a precursor for the support) dissolved in water to give a water-insoluble compound and if desired, shaping and/or calcinating the compound thus precipitated, or a method which comprises soaking an inorganic compound to become the support in an aqueous solution containing a metal ion to become the electrode material to impregnate the inorganic compound with the metal ion and precipitating the metal ion as a water-insoluble compound.

Electrode materials using a resin as a support may be prepared by various methods such as a method comprising adhering the electrode material to the surface of a shaped resin with an adhesive to coat to surface of said resin with the electrode material, a method comprising treating the surface of a shaped resin with a solvent or by heating, followed by adhering the electrode material to the surface of said resin, and a method comprising mixing a resin and the electrode material, shaping the mixture, and if desired, treating the surface. In addition, there may be employed a method comprising depositing the electrode material on the surface of other material by plating, vacuum vapor deposition, ion plating, or the like and fixing the electrode material thereto.

When the voltage applied across the electrodes is high, the decomposition velocity of hydrogen peroxide become high, but there occurs possibly other electrolysis, for example, electrolysis of sodium chloride. On the contrary, when the voltage is low, the decomposition velocity becomes low to take a long time for the decomposition.

Therefore, the voltage applied across the electrodes is preferably larger than the theoretical hydrogen peroxide decomposition voltage determined by the composition of the aqueous solution and the electrode material and simultaneously within the range of voltage where any other electrolysis does not occur. The voltage is preferably 0.5–10 V, more preferably 1.0–5.0 V. The power source may be d.c. or a.c., and is preferably d.c. As the direct current power source, there may be used, for example, dry cell, battery, solar cell, direct current converted from commercial alternating current (a.c.→d.c.). As alternating current, there is ordinarily used a commercial alternating current lowered to a desired voltage. An optional frequency can be used.

The time necessary for electrolysis of the remaining hydrogen peroxide may be optionally set on, for example, from several tens minutes to several hours or more depending on the size of electrode and the power source voltage. It is practically satisfactory that the remaining hydrogen peroxide is decomposed and removed until the concentration becomes about several tens ppm.

According to the method of the present invention, the following procedures may be carried out, for example, contact lenses are soaked in an aqueous hydrogen peroxide in a vessel provided with electrodes across which voltage is applied to treat the contact lenses while the hydrogen peroxide is decomposed and removed, or contact lenses are soaked in an aqueous hydrogen peroxide in a vessel provided with electrodes for a desired period of time to treat the contact lenses and then voltage is applied across the electrodes to decompose and remove the hydrogen peroxide.

As a modification of the latter, contact lenses are soaked in an aqueous hydrogen peroxide in a vessel provided with electrodes for a desired period of time to treat the contact lenses, then the aqueous hydrogen peroxide used for the treatment is discarded and a physiological saline solution is added to the contact lenses followed by applying voltage across the electrodes to dissolve out and decompose the still remaining, small amount of hydrogen peroxide. According to this method, the treating time can be more shortened.

The contact lenses thus treated are taken out and can be directly used to wear, or if desired, may be washed again with a physiological saline solution and then used to wear.

The physiological saline solution as mentioned above contains an amount of a salt which makes the aqueous solution substantially isotonic to tear liquid of man having 200–400 milliosmotic pressure (m Os) mole/kg, and this is usually a 0.7–1.4 weight % aqueous solution of sodium chloride. Such physiological saline solution may contain an antiseptic usable for ophthalmic purpose such as sodium thimerosal, sorbic acid, sodium sorbate, methyl paraben, chlorobutanol, benzalkonium chloride, acetic acid, phenyl mercury acetate and like.

According to the present invention, hydrogen peroxide remaining upon treating contact lenses with hydrogen peroxide can be decomposed and reduced quantitatively to a desired level. Therefore, the present invention provides a laborsaving and easy treatment of contact lenses as compared with conventional methods and is very convenient to the users of contact lenses. In addition, the electrode material used for electrolysis is stable to water, and therefore, substantially any material is not dissolved into the aqueous solution from the electrode. As a result, when the contact lenses thus treated are worn again, eyes are neither hurt nor irritated, and the contact lenses are safe.

In addition, said electrode can be prepared by simple methods or steps, and is inexpensive and of a long life.

As mentioned above, the present invention is very valuable from the practical point of view. The invention will be better understood in view of the following examples.

EXAMPLE 1

Treatment of soft contact lenses and decomposition of hydrogen peroxide:

Two soft contact lenses which were worn on two eyes of a man for about 10 hours and the surfaces of which whitened somewhat and had mucous matters attached thereto were soaked in 10 ml of an aqueous solution composed of 3 weight % hydrogen peroxide - 0.9 weight % sodium chloride, and simultaneously two platinum wires, each having a surface of 2.512 cm$^2$ (the distance between the electrodes being 2 cm) were soaked in the aqueous solution and d.c. voltage of 3 V was impressed across the electrodes. Then it was observed that bubbles were generated vigorously from the platinum electrode and hydrogen peroxide was rapidly decomposed.

The electric circuit was stopped 6 hours later and the two soft contact lenses were taken out of the aqueous solution. Then it was found that the white material present on the surface of each contact lens before the treatment completely disappeared and simultaneously the mucous material also disappeared. When a man wore the soft contact lenses on eyes, there was no feeling of unfitness. In view of the foregoing, it was confirmed that the contact lenses were successfully treated.

Analysis of the treating liquid:

The remaining hydrogen peroxide and metal ion in the treating liquid after the treatment were analyzed by an enzyme method and an I C P emission spectroanalysis, respectively, to give the results as shown in Table 1 (infra). The results clearly indicate that the hydrogen peroxide was substantially decomposed and removed and further the platinum electrodes were substantially water-insoluble.

EXAMPLE 2

The procedure of Example 1 was repeated except that the contact lenses were not soaked. The result is shown in Table 1.

COMPARATIVE EXAMPLE 1

The procedure of Example 2 was repeated except that any voltage was not impressed. A small amount of bubbles was generated at the surface of the platinum wire and hydrogen peroxide was somewhat decomposed.

In six hours, the concentration of hydrogen peroxide was measured and it was found that a considerable amount of hydrogen peroxide was still present and the catalytic action of the platinum wire itself was much less than electrolysis. The result of analysis of the aqueous solution is shown in Table 1.

EXAMPLES 3 and 4

The procedure of Example 2 was repeated except that the electrode materials as shown in Table 1 were used in place of platinum wire, the amounts of the solvent were ten times the amount in Example 2 and the voltages as shown in Table 1 were impressed. The result is shown in Table 1.

COMPARATIVE EXAMPLES 2 and 3

Procedures in Examples 3 and 4 were repeated, respectively, except that any voltage was impressed. The result is shown in Table 1.

TABLE 1

| | Electrode Material | | Surface Area of Electrode | Voltage | Amount of Washing Liquid | Analysis of Treating Liquid | | |
|---|---|---|---|---|---|---|---|---|
| | ⊕ | ⊖ | ⊕/⊖ (cm$^2$) | (V) | (ml) | Pt | Ni | H$_2$O$_2$ (ppm) |
| Example 1 | Pt | Pt | 2.512/2.512 | 3.0 | 10 | ND | — | 4 |
| Example 2 | Pt | Pt | 2.512/2.512 | 3.0 | 10 | ND | — | 4 |
| Comparative Example 1 | Pt | Pt | 2.512/2.512 | 0 | 10 | ND | — | 4142 |
| Example 3 | C | C | 28.26/28.26 | 6.0 | 100 | — | — | 15 |
| Comparative Example 2 | C | C | 28.26/28.26 | 0 | 100 | — | — | 25852 |
| Example 4 | Pt | Ni | 12.18/56.40 | 6.0 | 100 | ND | ND | 32 |
| Comparative Example 3 | Pt | Ni | 12.18/56.40 | 0 | 100 | ND | 0.03 | 26353 |

The initial concentration of hydrogen peroxide in the treating liquid was 30,000 ppm and the final concentration was that after 6 hours. "ND" indicates that said metal was not detected. Limit of detection by ICP emission spectroanalysis: Pt 0.4 ppm; Ni 0.03 ppm. The distance between electrodes is 2 cm in each case.

We claim:

1. A method for treating a contact lens with hydrogen peroxide in which the contact lens is soaked in an aqueous hydrogen peroxide in a vessel provided with electrodes to treat the contact lens and then voltage is applied across the electrodes to decompose and remove the remaining hydrogen peroxide.

2. The method according to claim 1 in which an electrode material used for the electrolysis is selected from the group consisting of platinum, gold, carbon, and graphite.

3. The method according to claim 1 or 2 in which the electrolysis is conducted with a voltage higher than the theoretical hydrogen peroxide decompositing voltage and incapable of causing electrolysis of materials other than hydrogen peroxide.

4. The method according to claim 3 in which the voltage is 0.5–10 V.

5. The method according to claim 4 in which the voltage is 1.0–5.0 V.

6. The method according to claim 1 in which the contact lens is soaked in an aqueous hydrogen peroxide in a vessel provided with electrodes to treat the contact lens simultaneously with applying voltage to the electrodes to decompose and remove the hydrogen peroxide.

7. The method according to claim 1 in which the aqueous hydrogen peroxide is discarded after treating the contact lens and then a physidogical saline solution is added to the contact lens followed by applying voltage across the electrodes to decompose the hydrogen peroxide still remaining.

* * * * *

UNITED STATES PATENT AND TRADEMARK OFFICE
CERTIFICATE OF CORRECTION

PATENT NO. : 4,836,859
DATED : June 6, 1989
INVENTOR(S) : Konishi, A., et al.

It is certified that error appears in the above-identified patent and that said Letters Patent is hereby corrected as shown below:

Column 6, line 48, delete "any", replace therefor --no--.

Signed and Sealed this

Nineteenth Day of January, 1993

Attest:

DOUGLAS B. COMER

*Attesting Officer*　　　*Acting Commissioner of Patents and Trademarks*